(12) United States Patent
Domschke et al.

(10) Patent No.: US 6,255,360 B1
(45) Date of Patent: Jul. 3, 2001

(54) PROCESS FOR THE MANUFACTURE OF MOLDINGS

(75) Inventors: Angelika Maria Domschke, Duluth; Vimala Mary Francis, Suwanee, both of GA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/570,656

(22) Filed: May 15, 2000

(51) Int. Cl.$^7$ ................................ C08J 9/00; C12N 5/00; C12N 5/02
(52) U.S. Cl. .......................... 521/64; 435/395; 521/145; 521/149; 526/72; 526/246; 526/247; 526/320
(58) Field of Search ..................................... 526/246, 247, 526/72, 248, 320; 521/145, 149, 64; 435/395

(56) References Cited

U.S. PATENT DOCUMENTS

| 4,440,918 | * | 4/1984 | Rice et al. | 526/246 |
| 4,818,801 | * | 4/1989 | Rice et al. | 526/246 |
| 5,076,844 | | 12/1991 | Fock et al. | 106/35 |
| 5,994,133 | * | 11/1999 | Meijs et al. | 526/246 |
| 6,015,609 | | 1/2000 | Chaouk et al. | 428/308.4 |
| 6,060,530 | | 5/2000 | Chaouk et al. | 521/64 |

FOREIGN PATENT DOCUMENTS

| 0 882 746 A2 | 12/1998 | (EP) . |
| WO 00/49058 | 8/2000 | (WO) . |

* cited by examiner

*Primary Examiner*—Morton Foelak
(74) *Attorney, Agent, or Firm*—R. Scott Meece; Robert J. Gorman, Jr.

(57) ABSTRACT

The present invention relates to a process for the manufacture of porous polymers, wherein a polymerizable component comprising at least one free radically polymerizable unsaturated monomer of formula $$Q-X-A \quad (1),$$

wherein the variables are defined as described in the claims, is polymerized in the presence of a specific solvent mixture, and the resulting porous polymer, after removal of the solvent, is subjected to an aftertreatment in an acidic or basic medium. The polymers obtainable according to the invention are useful, for example, as substrates for the attachment and growth of mammalian cells and tissue and in particular as materials for the manufacture of biomedical devices and prostheses, including implanted devices.

25 Claims, No Drawings

PROCESS FOR THE MANUFACTURE OF MOLDINGS

The present invention relates to a process for the manufacture of porous polymers, to moldings, especially biomedical moldings such as in particular ophthalmic moldings obtainable by the process and to specific copolymers, in both porous and non-porous form, being particularly suitable for various biomedical applications.

WO96/31548 discloses a class of materials based on perfluoroalkylpolyether macromonomers, which in both their porous and non-porous forms can act as cell growth substrates and are suitable for use as biomaterials, particularly in ocular applications. The document also discloses perfluoroalkylpolyether-containing compositions copolymerized with comonomers including minor amounts of dihydroperfluorooctyl acrylate. Although the polymers of the prior art document are suitable for biomedical applications, they suffer limitations mainly due to their pronounced hydrophobicity. For example, the permeability of the polymers to proteins, nutrients and the like is often not completely satisfactory. In particular, the permeability to high molecular weight proteins (about 600000 Daltons and higher) is difficult to achieve with the prior art materials. Moreover, the optical quality of the known materials may be affected during handling under ambient air or in contact with the biological environment. The hydrophobic prior art materials in general show a dry out effect in air which means that they lose the optical transparency when exposed to air. An extensive equilibration process in alcohol/water mixtures is then necessary to regain the transparency which means a serious restriction concerning the handling and application of the materials. Moreover, the prior art materials tend to irreversibly absorb proteins which likewise affects the optical transparency of the materials. Accordingly, there is a demand for novel polymeric materials comprising a further improved biocompatibility as well as improved optical properties.

It now has surprisingly been found that novel porous polymers with a unique combination of biocompatibility with living tissue including a suitable surface topography that enhances cell growth, oxygen permeability, permeability to proteins and nutrients and optical transparency in vivo may be obtained by the process as outlined below.

The present invention therefore in one aspect relates to a process for producing a porous polymer comprising the steps of:
(a) forming a composition comprising
(i) a polymerizable component comprising at least one free radically polymerizable unsaturated monomer of formula $$Q-X-A \quad (1)$$

wherein Q is a radical of formula $$-\overset{O}{\underset{}{C}}-[NH-(alk)-O-\overset{O}{\underset{}{C}}]_t-\overset{}{\underset{R_3}{C}}=CH_2, \quad (2)$$

(alk) is linear or branched $C_2$–$C_{12}$-alkylene, $R_3$ is hydrogen or $C_1$–$C_4$-alkyl, and t is the number 0 or 1, X is a group —O—, —S— or —$NR_1$— and $R_1$ is hydrogen, $C_1$–$C_4$-alkyl or a radical A, and A is a radical of formula $$-[(CH_2)_a-(CHF)_b-(CF_2)_c-(CF)_d]-CF_2-R_2 \quad (3)$$
$$\phantom{-[(CH_2)_a-(CHF)_b-(CF_2)_c-}|(CF_2)_z-R_2$$

wherein $R_2$ is hydrogen or fluorine, a is an integer from 1 to 15, b is an integer from 0 to 6, c is an integer from 1 to 19, d is an integer of 0 or 1, and z is an integer from I to 12; and
(ii) a solvent system being capable of effecting phase separation in the polymer which is obtained upon polymerizing the polymerizable component according to (i);
(b) polymerizing said composition and thereby forming a two-phase system comprising a polymer phase and a discrete solvent phase both of which are intermingled,
(c) removing the discrete solvent phase and
(d) subjecting the polymer obtained to an aftertreatment in an acidic or basic medium.

$R_3$ is preferably hydrogen or methyl and most preferably hydrogen.

(alk) is preferably $C_2$–$C_6$-alkylene, more preferably $C_2$–$C_4$-alkylene and in particular ethylene.

The variable t preferably denotes the number 0.

Especially preferred radicals —Q correspond to the formula $$-\overset{O}{\underset{}{C}}-\overset{}{\underset{H, CH_3}{C}}=CH_2.$$

X is preferably a group —O— or —$NR_1$— and most preferably —O—.

Regarding formula (3) the term in rectangular brackets is to be understood as a statistic description of the respective radicals, that is to say, the sequence of the groups —$CH_2$—, —CHF—, —$CF_2$— and —CF[($CF_2$)$_z$—$R_2$] is not fixed in any way by said formula.

$R_2$ in formula (3) denotes preferably fluorine.

Variable a is preferably an integer from 1 to 4, more preferably 1 or 2 and in particular 1. Variable b is preferably an integer from 0 to 4 and in particular 0. Variable c is preferably an integer from 1 to 14, more preferably 1 to 9 and in particular 5 to 9. Variable d is preferably an integer of 0. Variable z is preferably an integer from 1 to 8, more preferably 1 to 4 and most preferably 1.

Variable A is preferably a radical of the formula $$-(CH_2)_a-(CF_2)_c-(CF[CF_3])_d-CF_2-R_2 \quad (3a),$$

wherein $R_2$ is hydrogen or fluorine, a is an integer of 1 or 2, c is an integer from 1 to 19, preferably 1 to 14 and in particular 1 to 9, and d is an integer of 0 or 1, in particular 0. In a particular preferred embodiment of the invention A is a radical of formula (3a) above, wherein $R_2$ is fluorine, a is an integer of 1, d is 0, and c is an integer of from 1 to 19, preferably 1 to 14, more preferably 1 to 9 and in particular 5 to 9.

The fluorine-containing moiety A advantageously contains a fluorine to hydrogen ratio of greater than 50%, preferably of greater than 80%, and most preferably of greater than 90%.

Examples of particularly preferred compounds of formula (1) are 1H,1H,2H,2H-heptadecafluorodecyl acrylate, 1H,1H,9H-hexadecafluorononyl acrylate, 1H,1H-pentadecafluorooctyl acrylate, 1H,1H,2H,2H,- tridecylfluorooctyl acrylate, 1H, 1H-heptafluorobutyl acrylate, 1H, 1H-undecylfluorohexyl acrylate, 2-(perfluoro-7-methyloctyl)ethyl acrylate, or 2-(perfluoro-9-methyldecyl)ethyl acrylate. It is preferable that the length of the perfluorinated chain be 6 to 10 carbons long to obtain a material with a refractive index similar to tear film. However, this does not preclude the use of a combination of different length perfluorinated chains, ie less than 6 and greater than 10 to result in a material that has a refractive index similar to tear film or the use of perfluorinated chains greater than 10 carbons in order to counteract the high refractive indexes of other additives in the formulation. Also in some non-ocular applications matching refractive index of the material to tear film may not be important and hence the perfluorinated chain length may be outside the preferred range.

The polymerizable component used in the process of the invention may contain one or more different monomers of formula (1), preferably at least two different monomers of formula (1), more preferably 2 to 4 different monomers of formula (1) and in particular 2 different monomers of formula (1). The amount of monomer(s) of formula (1) used in the polymerizable component is, for example, in the range of from 15 to 100%, advantageously in the range from 20 to 90%, preferably in the range of 25 to 80%, more preferably in the range of 40 to 70% and particularly preferably in the range of 40 to 60% in each case by weight of the entire polymerizable component.

In addition to one or more different monomers of formula (1), further compounds comprising one or more ethylenically unsaturated groups, for example crosslinkers or comonomers, may be incorporated into the polymerizable component which can enter into a reaction to form the polymers of the invention. It is preferred that the ethylenically unsaturated group be selected from the group consisting of acryloyl, methacryloyl, styryl, acrylamido, acrylamidoalkyl, or urethanemethacrylate, or any substituted derivatives thereof.

The polymerizable component employed in step (a) preferably comprises one or more different crosslinkers. One group of suitable crosslinkers comprises a macromonomer of formula

$$Q_1—(PFPE—L)_{n-1}—PFPE—Q_1 \quad (4),$$

wherein n is $\geq 1$, each PFPE may be the same or different and is a perfluorinated polyether of formula

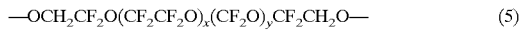

$$—OCH_2CF_2O(CF_2CF_2O)_x(CF_2O)_yCF_2CH_2O— \quad (5)$$

wherein the $CF_2CF_2O$ and $CF_2O$ units may be randomly distributed or distributed as blocks throughout the chain and wherein x and y may be the same or different such that the weight average molecular weight of the perfluoropolyether is in the range of from 500 to 4,000 and preferably from 500 to 2500;

L is a difunctional linking group; and $Q_1$ at each end of the macromonomer is the same or different and is a polymerizable group.

Preferably n is an integer from 1 to 4, and in particular of 1.

$Q_1$ is a polymerizable group which preferably contains an ethylenically unsaturated moiety which can enter into a polymerization reaction. Preferably the meanings and preferences given above for Q independently apply to $Q_1$. It is particularly preferred that $Q_1$ is acryloyl, methacryloyl or a radical —$C(O)NH—(CH_2)_{2-4}—O—C(O)—CR_5=CH_2$, wherein $R_5$ is hydrogen or methyl. $Q_1$ is most preferably acryloyl.

The linking group L may be any difunctional moiety able to react with hydroxyl. Suitable precursors to L are α,ω-diepoxides, α,ω-diisocyanates, α,ω-diisothiocyanates, α,ω-diacylhalides, α,ω-dithioacylhalides, α,ω-dicarboxylic acids, α,ω-dithiocarboxylic acids, α,ω-dianhydrides, α,ω-dilactones, α,ω-dialkylesters, α,ω-dihalides, α,ω-dialkylethers, α,ω-dihydroxymethylamides. It is preferred that the linking group be a bivalent residue —$C(O)—NH—R_6—NH—C(O)—$ of a diisocyanate wherein $R_6$ is a divalent organic radical having from 1 to 20 carbon atoms.

The divalent radical $R_6$ is, for example, alkylene, arylene, alkylenearylene, arylenealkylene or arylenealkylenearylene having 1 to 20 carbon atoms, a saturated bivalent cycloaliphatic group having 6 to 20 carbon atoms or cycloalkylenealkylenecycloalkylene having 7 to 20 carbon atoms.

In a preferred embodiment, $R_6$ is alkylene, arylene, alkylenearylene, arylenealkylene or arylenealkylenearylene having up to 14 carbon atoms or a saturated divalent cycloaliphatic group having 6 to 14 carbon atoms. In a particularly preferred embodiment, $R_6$ is alkylene or arylene having up to 12 carbon atoms or a saturated bivalent cycloaliphatic group having 6 to 14 carbon atoms.

In a preferred embodiment, $R_6$ is alkylene or arylene having up to 10 carbon atoms or a saturated bivalent cycloaliphatic group having 6 to 10 carbon atoms.

In a particularly preferred meaning, $R_6$ is a radical derived from a diisocyanate, for example from hexane 1,6-diisocyanate, 2,2,4-trimethylhexane 1,6-diisocyanate, tetramethylene diisocyanate, phenylene 1,4-diisocyanate, toluene 2,4-diisocyanate, toluene 2,6-diisocyanate, m- or p-tetramethylxylene diisocyanate, isophorone diisocyanate or cyclohexane 1,4-diisocyanate.

Aryl is a carbocyclic aromatic radical which is unsubstituted or substituted preferably by lower alkyl or lower alkoxy. Examples are phenyl, tolyl, xylyl, methoxyphenyl, t-butoxyphenyl, naphthyl and phenanthryl.

Arylene is preferably phenylene or naphthylene, which is unsubstituted or substituted by $C_1$–$C_4$-alkyl or $C_1$–$C_4$alkoxy, in particular 1,3-phenylene, 1,4-phenylene or methyl-1,4-phenylene, 1,5-naphthylene or 1,8-naphthylene.

A saturated bivalent cycloaliphatic group is preferably cycloalkylene, for example cyclohexylene or cyclohexylene ($C_1$–$C_4$-alkylene), for example cyclohexylenemethylene, which is unsubstituted or substituted by one or more $C_1$–$C_4$-alkyl groups, for example methyl groups, for example trimethylcyclohexylenemethylene, for example the bivalent isophorone radical.

Alkylene has 1 to 12 carbon atoms and can be straight-chain or branched. Suitable examples are decylene, octylene, hexylene, pentylene, butylene, propylene, ethylene, methylene, 2-propylene, 2-butylene, 3-pentylene, and the like. Particularly preferred meanings of alkylene are propylene, ethylene and methylene.

The arylene unit in alkylenearylene or arylenealkylene is preferably phenylene, unsubstituted or substituted by $C_1$–$C_4$-alkyl or $C_1$–$C_4$-alkoxy, and the alkylene unit therein is preferably $C_1$–$C_4$-alkylene, such as methylene or ethylene, in particular methylene. These radicals are therefore preferably phenylenemethylene or methylenephenylene.

Arylenealkylenearylene is preferably phenylene($C_1$–$C_4$-alkylene)phenylene, for example phenyleneethylenephenylene or phenylenemethylenephenylene.

Some examples of preferred diisocyanates from which bivalent residue L is derived include trimethylhexamethylenediisocyanate (TMHMDI), isophorone diisocyanate (IPDI), methylenediphenyl diisocyanate (MDI) and 1,6-hexamethylene diisocyanate (HMDI).

Preferably, x in formula (5) is in the range of from 0 to 20, more preferably from 2 to 16, and in particular from 4 to 12 and y is in the range from 0 to 25, more preferably from 4 to 20 and in particular from 6 to 14. Preferably, x and y may be the same or different such that the weight average molecular weight of the perfluoroalkyl polyether is in the range of from 500 to 2,500 and most preferably in the range of from 1000 to 2200.

A preferred crosslinker of the polymerizable component according to (a) is a macromonomer of the formula

wherein

PFPE is a perfluorinated polyether of formula

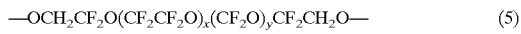

wherein the $CF_2CF_2O$ and $CF_2O$ units may be randomly distributed or distributed as blocks throughout the chain and wherein x and y may be the same or different such that the molecular weight of the perfluoroalkyl polyether is in the range of from 500 to 2,500;

and $Q_1$ is the methacryloyl radical $—C(O)—C(CH_3)=CH_2$ or preferably the acryloyl radical $—C(O)—CH=CH_2$.

A further group of suitable crosslinkers which may be used in the process of the invention are low molecular weight di- or polyvinylic crosslinking agents such as allyl (meth)acrylate, a $C_2–C_8$-alkylene diacrylate or dimethacrylate, divinyl ether, divinyl sulfone, di- and trivinylbenzene, trimethylolpropane triacrylate or trimethacrylate, pentaerythritol tetraacrylate or tetramethacrylate, bisphenol A diacrylate or dimethacrylate, methylene bisacrylamide or -bismethacrylamide, ethylene bisacrylamide or ethylene bismethacrylamide, triallyl phthalate, diallyl phthalate, or a compound of the formula

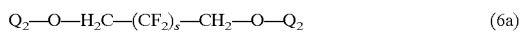

or

wherein for $Q_2$ independently the meanings and preferences given above for Q apply, s is an integer from, for example, 1 to 10, and preferably from 4 to 8, and q is an integer from, for example, 1 to 20 and preferably from 1 to 4.

The crosslinker is advantageously a low-molecular weight crosslinker having a weight average molecular weight of <1000, preferably of <750 and more preferably of <500.

Preferred low-molecular weight crosslinker components of the polymerizable component according to (a) are a compound of formula (6b) above, for example mono- di-, tri- or tetraethylene glycol diacrylate or mono-, di-, tri- or tetraethylene glycol diurethane methacrylat, or especially a fluorinated compound of formula (6a) above, for example 2,2,3,3,4,4-hexafluoropentanediol diacrylate or -dimethacrylate or 2,2,3,3,4,4,5,5-octafluorohexanediol diacrylate or -dimethacrylate.

The polymerizable component may contain one or more different crosslinkers, preferably one or two different crosslinkers. In one preferred embodiment of the invention there is used a polymerizable component according to step (a) comprising one sole crosslinker which is a macromonomer of the above formula (4) or (4a). In another preferred embodiment of the invention there is used a polymerizable component according to step (a) comprising two different crosslinkers, one macromonomer of the above formula (4) or (4a) and one of the above-mentioned low-molecular weight crosslinkers, preferably a crosslinker of formula (6a) or (6b) above, wherein each the above-given meanings and preferences apply.

The total amount of crosslinker(s) used is, for example, in the range of from 2 to 85%, preferably of from 10 to 80%, more preferably of from 20 to 75%, even more preferably of from 30 to 60% and particularly preferably of from 40 to 60%, in each case by weight of the entire polymerizable component.

A comonomer present in the polymerizable component can be hydrophilic or hydrophobic or a mixture thereof. Suitable comonomers are, in particular, those which are usually used in the production of contact lenses and biomedical materials. A hydrophobic comonomer is taken to mean a monomer which typically gives a homopolymer which is insoluble in water and can absorb less than 10% by weight of water. Analogously, a hydrophilic comonomer is taken to mean a monomer which typically gives a homopolymer which is soluble in water or can absorb at least 10% by weight of water.

Suitable hydrophobic comonomers are, without limitation thereto, $C_1–C_{18}$-alkyl and $C_3–C_{18}$-cycloalkyl acrylates and methacrylates, $C_3–C_{18}$-alkylacrylamides and -methacrylamides, acrylonitrile, methacrylonitrile, vinyl $C_1–C_{18}$-alkanoates, $C_2–C_{18}$-alkenes, $C_2–C_{18}$-haloalkenes, styrene, ($C_1–C_8$-alkyl)-styrenes, fluorinated styrenes, $C_1–C_8$-alkyl vinyl ethers, $C_3–C_{12}$-perfluoroalkylethylthiocarbonylaminoethyl acrylates and methacrylates, acryloxy- and methacryloxyalkylsiloxanes, N-vinylcarbazole, $C_1–C_{12}$-alkyl esters of maleic acid, fumaric acid, itaconic acid, mesaconic acid and the like.

Preference is given, for example, to acrylonitrile, $C_1–C_4$-alkyl esters of vinylically unsaturated carboxylic acids having 3 to 5 carbon atoms or vinyl esters of carboxylic acids having up to 5 carbon atoms.

Examples of suitable hydrophobic comonomers are methyl acrylate, ethyl acrylate, propyl acrylate, isopropyl acrylate, cyclohexyl acrylate, 2-ethylhexyl acrylate, methyl methacrylate, ethyl methacrylate, propyl methacrylate, butyl acrylate, vinyl acetate, vinyl propionate, vinyl butyrate, vinyl valerate, styrene, perfluorostyrene, chloroprene, vinyl chloride, vinylidene chloride, acrylonitrile, 1-butene, butadiene, methacrylonitrile, vinyltoluene, vinyl ethyl ether, perfluorohexylethylthiocarbonylaminoethyl methacrylate, isobornyl methacrylate, trifluoroethyl methacrylate, hexafluoroisopropyl methacrylate, hexafluorobutyl methacrylate, tristrimethylsilyloxysilylpropyl methacrylate (hereinafter: Tris methacrylate), tristrimethylsilyloxysilylpropyl acrylate (hereinafter: Tris acrylate), 3-methacryloxy propylpentamethyidisiloxane and bis(methacryloxypropyl) tetramethyidisiloxane.

Preferred examples of hydrophobic comonomers are methyl methacrylate, Tris acrylate, Tris methacrylate and acrylonitrile.

Suitable hydrophilic comonomers are, without this being an exhaustive list, hydroxyl- or amino-substituted $C_1–C_8$-alkyl acrylates and methacrylates, acrylamide, methacrylamide, ($C_1$-$C_8$-alkyl)acrylamides and methacrylamides, ethoxylated acrylates and methacrylates, hydroxyl-, amino- or sulfo-substituted ($C_1$-$C_8$-alkyl) acrylamides and -methacrylamides, hydroxyl-substituted $C_1$-$C_8$-alkyl vinyl ethers, acrylic or methacrylic acid, N-vinylpyrrole, N-vinyl-2-pyrrolidone, 2-vinyloxazoline, 2-vinyl-4,4'-dialkyloxazolin-5-one, 2- and 4-vinylpyridine, allyl alcohol, zwitterionic monomers such as a N-alkylacrylamide or N-alkylmethacrylamide comprising a quaternized amino group and a sulfonic acid group in the alkyl moiety, and the like.

Examples of suitable hydrophilic comonomers are hydroxyethyl methacrylate (HEMA), hydroxyethyl acrylate, hydroxypropyl acrylate, acrylamide, methacrylamide, N,N-dimethylacrylamide (DMA), N,N-dimethylaminoethyl methacrylate (DMAEMA), trimethylammonium-2-hydroxypropylmethacrylate hydrochloride, 3-[(2-acrylamido-2-methyl-propyl)-dimethylamino]-propanesulfonate, 2-acrylamido-2-methylpropanesulfonic acid (AMPS), allyl alcohol, vinylpyridine, glycerol methacrylate, N-(1,1-dimethyl-3-oxobutyl)acrylamide, N-vinyl-2-pyrrolidone (NVP), and the like.

Preferred hydrophilic comonomers are 2-hydroxyethyl methacrylate, N,N-dimethylacrylamide, N,N-dimethylaminoethyl methacrylate 3-[(2-acrylamido-2-methyl-propyl)-dimethylamino]-propanesulfonate and N-vinyl-2-pyrrolidone.

The preferred range for addition of individual comonomers into the polymerizable component is from 0 to 60% by weight and most preferably 0 to 40% by weight of the entire polymerizable component. In a preferred embodiment of the polymers of the invention, the underlying polymerizable component is devoid of a comonomer. In another embodiment of the polymers of the invention, the underlying polymerizable component comprises from 1 to 60% or in particular from 1 to 40% by weight of the entire polymerizable component of one or more different comonomers, where the above meanings and preferences apply.

A preferred embodiment of the invention relates to a process, wherein the polymerizable component according to (a) comprises
(i) at least two different monomers of formula

and
(ii) one or more, preferably two, different crosslinkers selected from the group consisting of a compound of formula

a compound of formula

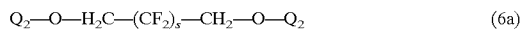

and
a compound of formula

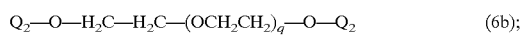

wherein Q, $Q_1$ and $Q_2$ are each independently of the other a radical of formula

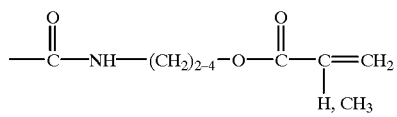

or in particular

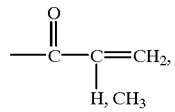

A is a radical of formula

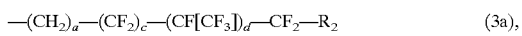

$R_2$ is hydrogen or fluorine, a is an integer of 1 or 2, c is an integer from 1 to 9 and d is 1 or preferably 0;
X is —O—, —NH— or —N($C_1$-$C_2$-alkyl), in particular —O—;
PFPE is a radical of formula

wherein the $CF_2CF_2O$ and $CF_2O$ units may be randomly distributed or distributed as blocks throughout the chain, and x and y may be the same or different such that the weight average molecular weight of the perfluorinated polyether is in the range of from 500 o 2500, s is an integer from 4 to 8, and q is an integer from 1 to 4.

The solvent system (ii) of the composition according to step (a) suitably comprises at least two components selected from the group consisting of a non-solvent, an intermediate solvent and a solvent for the respective polymerizable component (i).

A non-solvent means a liquid in which none of the components of the polymerizable component is soluble. The criterion that a component is insoluble in a liquid denotes in particular that the component is soluble in a concentration of <5% by weight, preferably <3% by weight, in said liquid. An intermediate solvent means an organic liquid in which some of the components of the polymerizable component, but not all, are soluble. A solvent means an organic liquid in which most or all of the components of the polymerizable component are soluble. The criterion that a component is soluble in a liquid denotes in particular that the component is soluble in a concentration of >5% by weight, preferably >10% by weight, in said liquid.

The types and amounts of solvents, intermediate solvents and/or non-solvents depend to a great extent on the types and amounts of components used in the polymerizable component but may be determined by simple experiment.

Suitable non-solvents are typically highly polar solvents such as DMSO, acrylonitrile or in particular water.

A suitable intermediate solvent is, for example, a polar solvent and is preferably selected from the group consisting of short chain alcohols, amines, nitrites and carboxylic acids, and mixtures thereof. The said short chain alcohols, amines, nitrites, and carboxylic acids may be cyclic, branched or linear; branched chain compounds are particularly preferred. The number of carbon atoms within the short chain compound may be from 1–12; it is preferred however that the number is from 2–8. Preferred intermediate solvents are amines having up to 12 carbon atoms, alcohols of up to 12 carbon atoms, preferably non-fluorinated alcohols, ethers of up to 12 carbon atoms, nitriles of up to 12 carbon atoms, carboxylic acids of up to 12 carbon atoms. More preferred intermediate solvents are non-fluorinated $C_1$–$C_{10}$-alkanols, such as methanol, ethanol, n- or isopropanol, 3-methyl-2-butanol, cyclohexanol or cyclopentanol, $C_1$–$C_{10}$-amines, such as 3-hexylamine and isopropylamine, $C_1$–$C_{10}$-nitriles, such as acetonitrile, or $C_1$–$C_{10}$-carboxylic acids, such as acetic acid, and even more preferred are such non-solvents having up to 7 carbon atoms. Further preferred are non-fluorinated $C_1$–$C_{10}$-alkanols, $C_1$–$C_{10}$-amines, $C_1$–$C_{10}$-nitriles and $C_1$–$C_{10}$-carboxylic acids, and even more preferred are such intermediate solvents having up to 7 carbon atoms. Especially preferred as intermediate solvent are $C_1$–$C_4$-alcohols such as in particular methanol, ethanol or n- or isopropanol.

The solvent component of the solvent system according to step (a) may be essentially any organic liquid in which most or all of the components of the polymerizable component is soluble in. The solvent is, for example, a non-polar solvent, for example a hydrocarbon solvent, a ketone or an ether each having up to 12 carbon atoms which may be cyclic, branched or linear, and which may be substituted by $C_1$–$C_4$-alkyl, $C_1$–$C_4$-alkoxy or halogen, such as methyl, ethyl, methoxy, fluoro or chloro. Preferred such non-polar solvents are a $C_5$–$C_{12}$-alkane, $C_5$–$C_{12}$-cycloalkane, benzene, $C_3$–$C_{10}$-ether or $C_3$–$C_{10}$-ketone each of which unsubstituted or substituted by $C_1$–$C_4$-alkyl, $C_1$–$C_4$-alkoxy or halogen. Examples are cyclohexane, p-fluoromethoxy benzene, cyclohexanone, p-fluorobenzene methyl ketone or perfluorinated ethers such as for example HFE 7100 (3M).

The amount of non-solvent is, for example, up to 10%, preferably from 0 to 10%, more preferably from 0 to 5%, and most preferably from 0.1 to 2.5%, in each case by weight of the total solvent system.

The amount of intermediate solvent is, for example, up to 95%, preferably from 30 to 90%, and most preferably from 40 to 80%, in each case by weight of the total solvent system.

The amount of solvent is, for example, up to 75%, more preferably 10 to 70%, and most preferably 20 to 60%, in each case by weight of the total solvent system.

A preferred solvent system in step (a) of the process of the invention comprises 0 to 5% by weight of water, 30 to 90% by weight of an intermediate solvent selected from the group consisting of a non-fluorinated $C_1$–$C_{10}$-alkanol, a $C_1$–$C_{10}$-amine, a $C_1$–$C_{10}$-nitrile and a $C_1$–$C_{10}$-carboxylic acid; and 10 to 70% by weight of a solvent selected from the group consisting of a hydrocarbon having up to 8 carbon atoms, a fluorinated hydrocarbon having up to 8 carbon atoms, and a $C_1$–$C_{10}$-ketone.

The composition according to step (a) of the invention contains the polymerizable component (i) and the solvent system (ii) in a weight ratio of, for example, from 90%:10% to 10%:90% respectively, preferably of from 90%:10% to 40%:60%, and most preferably of from 85%:15% to 50%:50%.

In addition to the polymerizable component and the mixture of organic liquids, the composition according to step (a) may contain optional further ingredients. Optional further ingredients of the composition according to step (a) are for example:
(i) photoinitiators; in case of a photochemical initiation of the polymerization reaction according to step (b) it is preferred to add a photoinitiator. Examples thereof are familiar to the person skilled in the art. Useful photoinitiators include for example benzophenones substituted with an ionic moiety, a hydrophilic moiety or both such as 4-trimethylaminomethyl benzophenone hydrochloride or benzophenone sodium 4-methanesulfonate; benzoin $C_1$–$C_4$-alkyl ether such as benzoin methyl ether; thioxanthones substituted with an ionic moiety, a hydrophilic moiety or both such as 3-(2-hydroxy-3-trimethylaminopropoxy) thioxanthone hydrochloride, 3-(3-trimethylaminopropoxy) thioxanthone hydrochloride, thioxanthone 3-(2-ethoxysulfonic acid) sodium salt or thioxanthone 3-(3-propoxysulfonic acid) sodium salt; or phenyl ketones such as 1-hydroxycyclohexylphenyl ketone, (2-hydroxy-2-propyl)(4-diethylene glycol phenyl)ketone, (2-hydroxy-2-propyl)(phenyl-4-butanecarboxylate)ketone; or commercial products such as Darocure™ or Irgacure™ types, e.g. Darocure 1173 or Irgacure 2959.

The photoinitiator, if added to the composition, is present in an amount of for example 0.05 to about 1.5% by weight, preferably 0.1 to 1.0% by weight and particularly preferably 0.08 to 0.5% by weight, based on the polymerizable component in each case.

(ii) surfactants; surfactants, preferably fluorinated surfactants may be incorporated into the mixture. The use of surfactants is an effective means of controlling the size and density of the pores. Non-ionic surfactants containing fluorine are preferred. Particularly preferred surfactants include commercially available fluorinated surfactants such as Zonyl (DuPont) and Fluorad (3M). Zonyl FS300 (DuPont) which is made up of a perfluorinated hydrophobic tail and hydrophilic poly(ethylene oxide) head group, is a particularly preferred surfactant for use in the process. The composition according to step (a) is preferably devoid of a surfactant.

The polymerizable component may be mixed with the organic solvent and other optional components by any convenient means. For example, the polymerizable component may be mixed with the organic solvent and other optional components by shaking or stirring. The order in which the components are added is not narrowly critical. The various components which make up the polymerizable component do not need to be combined prior to incorporation in the mixture. The mixture may be in the form of a homogeneous solution or may have the organic solvent as a distinct phase, such as in the form of a dispersion, microemulsion or preferably a co-continuous microemulsion. The form of the mixture prior to polymerization is not narrowly critical since it is the form of the mixture during polymerization which controls the morphology of the porous polymer.

The polymerization of the composition according to step (b) in general may be performed by any convenient method with reference to the initiation of the polymerizable component. For example, the polymerization may be triggered by actinic radiation, such as, for example, UV light, or by ionising radiation, such as, for example, gamma radiation, electron radiation or X radiation. The polymerization can where appropriate also be triggered thermally. Suitable polymerization conditions will be apparent to those skilled in the art. For example, temperatures may range from 0 to 80° C. or preferably from 5 to 50° C., and pressures may range from below atmospheric to above atmospheric. Oxygen-free conditions may be used. The polymerizable component is preferably polymerized in the presence of a photoinitiator using actinic radiation, in particular UV light. Curing times may vary within wide limits and depending on the light intensity employed. In general, a curing time of from 1 to 60 minutes, preferably from 2 to 30 minutes and in particular from 5 to 15 minutes, has proven as valuable.

Immediately after polymerization it is essential that a substantial proportion of the organic solvent is in the form of a discrete phase. The discrete organic solvent phase is preferably at least partly in the form of an interpenetrating network throughout the polymerized component.

It will be understood that by "a substantial proportion of the organic solvent is in the form of a discrete phase" we mean that there is sufficient organic solvent phase to form either an interpenetrating network of organic solvent phase or a dispersion of organic solvent phase. It will be understood by the person skilled in the art that depending on the polymerization component and the organic solvent a proportion of organic solvent may be adsorbed or retained in the polymerization component and eventually in the porous polymer. Typically more than 60% of the organic solvent is in the form of a discrete phase immediately after polymerization. It is preferred that greater than 80% of the organic solvent is in the form of a discrete phase, more preferably greater than 95% of the organic solvent is in the form of a discrete phase.

It is particularly preferred that the organic solvent phase forms an interpenetrating network in the polymerization component resulting in the porous polymer having a reticulated porous morphology. The reticulated porous morphology may have an open-cell structure with an array of interconnected generally spherical pores or, preferably may be an open-cell, sponge-like structure consisting of interconnected polymer globular particles.

In another embodiment the porous polymer may be in the form of a closed-cell structure with discrete pores dispersed throughout the polymer.

According to step (c), the organic solvent may be removed from the porous polymer by any convenient means. Suitable means for removal of solvent include evaporation, solvent extraction, washing or leaching.

The aftertreatment according to step (d) may be carried out in any medium that is suitable to convert pendant acrylate, acrylamide or the like groups on the surface of the porous polymer to acid/salt functionalities. Preferably the aftertreatment is carried out in an aqueous medium comprising an acid or preferably a base. Suitable acids are, for example, acetic acid, fluoro or chloroacetic acids, hydrochloric acid or sulfuric acid. Suitable bases are, for example, alkali metal hydroxides such as sodium or potassium hydroxide, ammonia or organic amines. In addition to water the aftertreatment medium may comprise additional solvents, for example a $C_1$–$C_4$-alcohol such as methanol, ethanol or n- or isopropanol.

One suitable aftertreatment medium comprises an acidic medium having a pH of, for example, from 1 to 6 and preferably from 1 to 4.5. A suitable acidic medium may be prepared, for example, from water or a mixture of water and a $C_1$–$C_4$-alcohol and an inorganic or preferably organic acid; examples are an aqueous solution comprising acetic, hydrochloric, sulfuric or the like acid. A preferred aftertreatment medium is a basic medium comprising a pH of, for example, from 8 to 14 and preferably from 8.5 to 12. A suitable basic medium may be prepared, for example, from water or from water and a $C_1$–$C_4$-alcohol and a suitable organic or preferably inorganic base; examples are an aqueous solution or a water/ethanol solution comprising in each case an alkali hydroxide such as sodium or potassium hydroxide or a mixture thereof or comprising ammonia or an organic amine as the base. A preferred basic aftertreatment medium is an aqueous medium comprising from 20 to 60% by weight of an alkali hydroxide, in particular sodium hydroxide.

The aftertreatment may be carried out, for example, at room temperature or at elevated temperature, such as at a temperature from 15 to 100° C., preferably from 20 to 80° C. and in particular from 30 to 60° C. The porous polymers are, for example, simply dipped in the aftertreatment medium or may also be treated using ultrasound to effect hydrolysis.

The duration of the aftertreatment according to step (d) may vary within wide limits depending, for example, on the temperature and pH of the solution employed. In general, a time period of from 30 seconds to 1 hour, preferably of from 30 seconds to 30 minutes and in particular of from 30 seconds to 3 minutes has proven as valuable.

Prior to the aftertreatment according to step (d) the porous polymers obtained according to step (c) may be treated with an alcoholic solution, for example with an aqueous solution comprising from 10 to 50% by weight of a $C_2$–$C_4$-alcohol such as ethanol or isopropanol, or with a solution comprising a surfactant, in particular a non-ionic surfactant, in order to ensure a better reaction between the hydrophobic polymer and the hydrophilic acidic or basic aftertreatment solution.

The process of the present invention is useful for generating materials of various pore sizes and morphologies. The upper limit of average pore size of individual pores is about 5 microns, with 100 nanometers being typical, while pores of around 10 nanometers in diameter may also be obtained.

The pores may form an interpenetrating network. It is more useful to characterise these morphologies in terms of permeability to molecules of defined molecular weight.

The morphology and porosity of the porous polymer may be controlled by altering the ratio of the organic solvent to the monomer. At high ratios of organic solvent, an open sponge-like structure consisting of interconnected polymer globular particles is obtained. At lower ratios, a reticular network of pores is obtained. At even lower ratios a closed-cell morphology is obtained.

In addition, the etching step (d) of the claimed process allows to tailor the surface topography of the resulting polymer in order to meet the requirements of a specific application. The type of etching has a direct bearing on the surface structure which can be fibrous or smooth. For example, by modulating the etching process a fibrous surface structure can be obtained that mimics the Bowman's membrane of the eye. In addition, since the design of the surface topography has a great relevance in the process of cell anchoring, spreading and stratification, the process of the invention allows to manufacture polymer materials which are extremely efficient as cell growth substrates.

Particularly useful embodiments of the present method have the organic solvent phase in the form of a continuous interpenetrating network structure which may be readily extracted to leave a porous perfluorinated polymeric material having a reticular network of pores allowing ready passage of fluid and small diameter particles through the porous polymer.

The size and density of the pores may be controlled by the ratio of the polymerizable component to organic solvent or by changes of the composition of the solvent. Minor changes can be effected by the use of surfactants. The addition of a minor proportion of water also increases porosity.

With suitable selection, the resultant copolymers are optically transparent, having a refractive index that provides a good match with aqueous media, tissue and cellular material. Most important, due to the specific aftertreatment the optical quality of the polymeric materials obtainable according to the process of the invention remains high during handling under ambient air and in contact with the biological environment. As a result the polymers obtainable according to the invention are ideal for use as an ophthalmic device or a ocular prostheses, such as a corneal onlay or implant.

A further embodiment of the invention relates to porous polymers obtainable according to the above-outlined process.

According to still a further aspect of the invention there is provided a polymer, either non-porous or porous, that is obtainable by polymerizing a polymerizable component comprising
(i) at least two different monomers of the above formula (1), and
(ii) one or more different crosslinkers,
wherein for the variables contained in formula (1), for the crosslinkers and for the weight ratios each the above-given meanings and preferences apply.

Non-porous polymers may be obtained from the above-mentioned polymerizable component in conventional manner, for example by copolymerizing the monomers of formula (1), the crosslinker(s) and optionally one or more comonomers and/or further additives to afford a transparent polymer in the presence of a suitable initiator. Standard methods well known in the art for effecting polymerization may be utilized, with free radical polymerization being preferred. Free radical polymerization can be simply carried out by radiating (using ultraviolet light) the polymerizable component containing a photoinitiator, such as benzoin methylether, in an appropriate container or vessel. The mixture is irradiated for a sufficient time to enable polymerization between monomers to take place. Alternatively, redox initiation or thermal initiation using a thermal initiator such as azobisisobutyronitrile, can be employed. Suitable optional comonomers and further additives are, for example, those mentioned before. The photochemical initiation of the monomer mixture using a photoinitiator is the preferred polymerization method.

A further embodiment of the invention relates to the use of the non-porous or porous polymers obtainable by the processes of the invention for the manufacture of moldings, in particular biomedical moldings in both ophthalmic and non-ophthalmic applications. Suitable moldings are, for example, biomedical devices, e.g. ophthalmic devices such as contact lenses, intraocular lenses or artificial cornea comprising a polymer of the invention. Preferred moldings of the invention are those obtainable by the above outlined process for the preparation of porous polymers.

The polymers of the present invention may be formed into other useful articles using conventional molding and processing techniques as are well known in the art. Given the visual transparency of the polymers of the present invention, they may find use in tissue culture apparatus, optical instruments, microscope slides and the like.

A further aspect of this invention is the use of the porous polymers obtainable according to the process of the invention in film or sheet form as a membrane or a filter. Such polymer films may be laminated with another support film to form a composite. Such applications may involve permeability to gases or liquids.

The porous polymers of the present invention may be suitable for use as a membrane having a variety of applications including industrial membranes, capacitors, home reverse osmosis, implanted glucose monitors, encapsulated biological implants e.g. pancreatic islets, drug delivery patches, membrane distillation using osmotic pressure, sustained release of active compounds, immobilised ligands for use in bioreactors or biosensors. Other applications include wound healing dressings, biotechnology and biomedical applications including vascular grafts, drug delivery patches, materials for the sustained release of active compounds and ultrafiltration in the food, dairy, juice, low alcohol beer industries.

As the polymers of the invention, whether porous or non-porous, are generally biocompatible towards cells and are of a chemistry that is chemically stable, these polymers can be enhanced for particular applications by applying to the surface of the polymers a surface coating. Such a surface coating can be a hydrophilic coating applied by a dip coating process or by RF gas plasma deposition method or the covalent attachment of particular chemical species or molecule; alternatively, such a coating can be a gel applied to the surface of a porous polymer. Such as a coating for the purpose of further enhancing the cell growth characteristics of the polymer can be the covalent attachment or adsorption of a molecule such as fibronectin, vitronectin, laminin, thrombospondin, or a peptide sequence fragment thereof, or the covalent attachment or adsorption of a gel comprising or containing these proteins.

The polymers obtainable according to the processes of the invention, whether non-porous or preferably porous, are capable of interacting with human or animal tissue cells and are thus particularly useful as materials for the attachment and growth of human or animal cells in vivo or in vitro, medical implants (such as implantable semipermeable membrane materials, tissue implants in cosmetic surgery, implants containing hormone secreting cells such as pancreatic islet cells, breast implants, artificial joints, and the like), in artificial organs, tissue culture apparatus (such as bottles, trays, dishes and the like), in biological reactors (such as those used in the production of valuable proteins and other components by cell culture), as material for the fabrication of medical devices or as coating for biomedical or biomaterial devices or applications, such as coatings on vascular grafts, catheters, artificial pancreas and the like, or as material for ophthalmic devices, such as contact lenses, intraocular lenses or artificial cornea, or ocular prostheses, such as corneal implants.

Ocular prostheses, such as corneal implants, may be made by polymerization of the polymerizable components in molds and, optionally, the resultant copolymer may be fabricated or machined to the desired conformation. Ocular prostheses may be made by other methods which are well known per se to those skilled in the art. Porosity may be provided as described above.

Corneal implants may be placed by way of conventional surgery techniques beneath, within, or through corneal epithelial tissue, or within the corneal stroma or other tissue layers of the cornea. Such implants may change the optical properties of the cornea (such as to correct visual deficiencies) and/or change the appearance of the eye, such as pupil coloration. A corneal implant may comprise an optical axis region which on implantation covers the pupil and provides visual acuity, and a less transparent region which surrounds the periphery of the optical axis region. Alternatively the implant may have the same visual acuity across its dimensions.

It has been found that the flow of high molecular weight tissue fluid components such as proteins and glycoproteins (for example, growth factors, peptide and protein hormones, and proteins associated with the transport of essential metals) and the like across a corneal implant, that is, between epithelial cells and stromal cells and even the endothelial layer and beyond, is important for long term maintenance and viability of tissue anterior and posterior to a corneal implant. By the process of the invention, in particular by means of the etching step (d), it is possible to regulate the surface topography and porosity towards a long term stability of the implant in vivo. Accordingly the corneal implant is advantageously prepared with a porosity sufficient to allow passage therethrough of tissue fluid components having a molecular weight greater than about 10,000 daltons, thereby providing for a flux of tissue fluid components in addition to small molecular weight nutrients (such as glucose, fats and amino acids) and respiratory gases between cells anterior of the implant and cells posterior thereof.

Preferably a corneal implant has a porosity sufficient to admit proteins and other biological macromolecules of a molecular weight up to and greater than 10,000 daltons, such as from 10,000 to 1,000,000 daltons, but not sufficient to admit cells and thus tissue invasion into the optical axis region of the corneal onlay. Where porosity of the implant is provided by pores, the optical axis region comprises a plurality of pores, the number of which is not in any way limiting, but which is sufficient to provide flow of tissue components between the anterior and posterior regions of an implant. Preferably, the pores formed within the optical axis region do not cause refraction of visible light to an extent that would cause any problem with regard to vision correction. It is to be understood that the term pore does not put any geometric limitation on the nature of the pores which may be of regular or irregular morphology. It should be recognized that not all pores may be of the same diameter.

Outside of the optical axis region, the corneal implant may have the same porosity as the optical axis region. Alternatively, this region of the implant surrounding the periphery of the optical axis region, which may be referred to as the skirt, may allow the ingrowth of cells of the cornea thereby assisting in anchorage of the implant to the eye.

Porosity in the skirt may be an inherent feature of the material from which the skirt is formed. In this regard it is to be appreciated that the skirt may be formed of the same material as the optical axis region and may be integral therewith. In this situation, pores of differing diameter may be formed in the optical axis region and the skirt. Alternatively, the skirt may be formed of a different material from the optical axis region, which material is of a higher porosity than the optical axis region so as to allow this tissue ingrowth. Preferably the skirt may be comprised of an optically transparent polymer as is the optical axis region, but alternatively, the skirt may be comprised of an optically non-transparent material or may be made of a porous material that is not optically transparent.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

The present invention is further described in the following non-limiting examples. If not otherwise specified, all parts are by weight. Temperatures are in degrees Celsius. Molecular weights of monomers or polymers are number average molecular weights if not otherwise specified.

EXAMPLE 1

5.25 g (22.7%, w:w) 1H,1H,2H,2H-heptadecaperfluorodecyl acrylate (Monomer-Polymer & Dajac), 5.25 g (22.7%, w:w) 1H,1H-pentadecaperfluorooctyl acrylate (Monomer-Polymer & Dajac), 0.68 g (2.9%, w:w) octafluorohexanediol-1,6-diacrylate (Monomer-Polymer & Dajac), 7.5 g (32.5%, w:w) polyperfluoroethyleneglycol diacrylate (Monomer-Polymer & Dajac), 2.5 g (10.9%, w:w) ethanol (Aldrich, anhydrous), 1.8 g (7.8%, w:w) cyclohexanone (Aldrich, 99.8%), 0.02 g (0.1%, w:w) distilled water and 0.1 g (0.4%, w:w) Darocure® 1173 are weight into a round bottom flask. The mixture is micro filtered (PTFE filter, pore size 0.45 mm) and transferred to a round-bottom flask with a nitrogen attachment. The oxygen dissolved in the mixture is removed by applying three times a freeze thaw process. This process involves the evacuation of the frozen mixture applying a negative pressure of 50 mtorr and subsequent thawing of the mixture with the flask sealed. The mixture is transferred into inert gas atmosphere. 100 $\mu$l each of this mixture is filled into one polypropylene mold . The molds are closed with an appropriate lid and the curing reaction is effected by UV irradiation (curing time 5 minutes, curing intensity 15 mW/cm$^2$). The molds are opened and the lenticules demolded in a 2-isopropanol bath. The resulting lenticules are extracted for 24 h at RT in constantly replenished distilled 2-isopropanol.

The extracted lenticules are equilibrated into distilled water in a three step procedure. Starting with a 20 minutes equilibration of each lenticule in a 2-isopropanol/water mixtures (75/25, v:v) followed by a 20 minutes equilibration in a 50/50, v:v mixture, a 20 minutes equilibration in a 75/25 v:v 2-isopropanol/water mixture and finally the equilibration into distilled water.

The surface modification is performed in 50% sodium hydroxide solution (Aldrich), at 40° C. for 60 seconds. The modified lenticules are placed into 700 ml of a 2-isopropanol/water mixture (15/85, v:v) at 40° C. and extracted for 15 hours. During this time the extraction medium is replaced three times. The extracted lenticules are transferred into distilled water and autoclaved (30 minutes, 221° C.).

EXAMPLES 2–4

Further porous moldings are prepared according to the method of example 1 using as polymerizable component a composition as outlined in the Table below:

TABLE (all data given in % by weight of the total composition)

| Ex. | hepta | penta | octa | poly | ethanol | cyclo-hexanone | water | initiator |
|-----|-------|-------|------|------|---------|----------------|-------|-----------|
| 2 | 21.9 | 23.3 | 2.6 | 33.0 | 10.7 | 8.0 | 0.1 | 0.4 |
| 3 | 22.5 | 22.6 | 3.0 | 32.2 | 11.1 | 7.8 | 0.1 | 0.7 |
| 4 | 22.4 | 22.3 | 3.0 | 31.9 | 11.2 | 8.2 | 0.5 | 0.5 | hepta = 1H,1H,2H,2H-heptadecaperfluorodecyl acrylate
penta = 1H,1H-pentadecaperfluorooctyl acrylate
octa = octafluorohexanediol-1,6-diacrylate
poly = polyperfluoroethyleneglycol diacrylate, $M_w$ = 1000 (Aldrich, anhydrous) (Examples 2,3); or a polyperfluoroethyleneglycol diacrylate, $M_w$ = 2000 (Example 4, synthesis see below)
initiator = photoinitiator (Darocure ® 1173)

The curing intensity in the procedure for example 2 is 15 mW/cm$^2$. The intensity applied for examples 3 and 4 is 6 and 12 mW/cm$^2$. The diffusion coefficients of the examples resemble that of example 1 within the measurement error margins.

Synthesis of the polyperfluoroethyleneglycol diacrylate, $M_w$=2000 used in Example 4:

Fomblin Z Dol TX (10 g, 0.0046 moles) from Aussimont is taken in a clean dry 250 ml round bottom flask with a stir bar and equipped with a water condensor. 100 ml of a fluoro solvent, HFE 7100 (3M) is added to Fomblin Z Dol TX and the contents are stirred to form a homogeneous mixture. The reaction flask is sealed with a rubber septum and the contents maintained under a slow nitrogen flow. The flask is immersed in an ice bath and the contents are allowed to cool for about 15 minutes. Acryloyl chloride (1.5 ml, 0.0185 moles) from Aldrich is added to the reaction flask in drops using a syringe. The homogeneous mixture turns slightly white in color after a few hours. The mixture is then allowed to stir overnight at room temperature. To ensure complete conversion to the product, the mixture is heated to 55° C. using an oil bath. The oil bath is maintained between 55° C. and 60° C. throughout the entire reaction time. The reaction is allowed to proceed for a week under a slow nitrogen flow.

The crude reaction mixture is allowed to cool and the contents are transferred into a separatory funnel. The mixture is washed with water (2×100 ml), followed by 10% HCl (2×100 ml), saturated NaHCO$_3$ (2×100 ml), and saturated NaCl (2×100 ml). At every step of the extraction process, the phases are allowed to separate slowly. When separation is difficult due to emulsion formation, saturated NaCl is added and the mixture is given enough time to separate. Finally the fluoro phase containing the product acrylate is separated into a clean flask and dried with magnesium sulfate. The contents are filtered and the solvent is removed under reduced pressure using a rotary evaporator. The final product is a white oil. The oil is filtered using a syringe filter (0.45 um) to yield a clear oil.

$^1$H NMR (C$_6$H$_5$CH$_3$): 3.4–3.8 ppm [approximately 20H, (CH$_2$CH$_2$O)$_n$) of Fomblin], 4.1–4.3 ppm (2H, CH$_2$ group adjacent to terminal acrylate, ie. CH$_2$=CH—CO—O—CH$_2$CF$_2$—), 5.5–6.4 (6H, CH$_2$ and CH groups of diacrylate).

$^{13}$C NMR (C$_6$H$_5$CH$_3$): 60–80 ppm [(CH$_2$CH$_2$O)$_n$) of Fomblin], 110–140 ppm (CF$_2$ group of Fomblin, acrylate group carbons, solvent peaks from C$_6$H$_5$CH$_3$), 165.6 ppm (ester peak ie., CH$_2$=CH—COO—).

Protein Permeation Test

The following technique, referred to herein as the "Multiple Protein Permeation Test", is used for the determination of the protein permeation of the lenses.

The Multiple Protein Permeation Test involves two major parts.
a HPLC set up equipped with size exclusion columns (Bioselect TM SEC 125-5), a UV detector and an autosampler (Shimadzu SIL 10AXL); and
a diffusion cell set up including a donor chamber (Crown Bio Scientific) which contains a mixture of 5 proteins (, thyro globulin, gamma globulin, ovalbumin, myoglobin, vitamin B-12 (Bio-Rad Gel filtration standard) dissolved in phosphate buffer at pH 6.8 and a receiving chamber (Crown Bio Scientific) filled with phosphate buffer at pH 6.8. The receiving chamber is equipped with an inlet and outlet tubing. The tubing's are connected by a especially designed flux vial placed in the autosampler. the buffer is constantly circulating though the receiving chamber and tubing by a peristaltic which is connected to the outlet tubing. Both chambers are kept at 35° C.

The donor and receiving chamber are connected by a lens holder which is especially designed for sealing a lens thereto, so that the donor solution does not pass around the lens (i.e., proteins may only pass through the lens). Proteins are diffusing though the lens into the receiving chamber on a concentration gradient. Small samples were taken every 20 minutes from the circulating system connected to the receiving chamber and injected in the size exclusion column. The increase of the concentration of the proteins with time gives the MPPT diffusion coefficient $D_{mppt}$ by applying the following formula:

$$D_{mppt}=(n'/\Delta c)\times(d/A)$$

where $D_{mppt}$=MPPT diffusion coefficient [mm$^2$/min];

n'=rate of proteins transport [mol/min]; A=area of lens exposed [mm$^2$];

$\Delta$c=concentration difference [mol/L]; d=thickness of the lens [mm];

The following Table shows diffusion coefficients obtained by this method for a lens obtained according to Example 1 and for different commercial membranes. The pore size varies from 15 to 100 nm. The diffusion coefficient of immunoglobulin and serum albumin in the cornea is 0.00042 and 0.00014 mm2/min. taken from D. M. Maurice, P. G. Watson, Exp. Eye Res. (1965), 355–363, M. Allansmith, A. de Ramus, D. Maurice, Assoc. for Res. in Vis. and Ophthal., Inc. (1979) 18, 947–955.

TABLE

Diffusion coefficient in mm$^2$/min for different proteins through commercial membranes and through the material of example 1:

| Proteins | molecular weight | Nucleo pore ® 100 nm | Nucleo pore ® 50 nm | Nucleo pore ® 15 nm | Lens of Example 1 |
|---|---|---|---|---|---|
| thyro globulin | 670000 | 2.9E-5 | 1.4E-5 | 2.6E-6 | 8.8E-5 |
| gamma globulin | 158000 | 7.9E-5 | 4.8E-5 | 3.1E-6 | 8.5E-5 |
| ovalbumin | 44000 | 1.3E-4 | 9.1E-5 | 6.1E-6 | 1.5E-4 |
| myoglobin | 17000 | 1.7E-4 | 1.4E-4 | 9.0E-6 | 1.2E-4 |
| vitamin B-12 | 1350 | 4.3E-4 | 3.4E-4 | 2.5E-5 | 2.6E-4 |

The data indicate that the polymer of Example 1 is porous towards molecules of molecular size up to that of thryo globulin, which is a protein of molecular weight of 670000.

Standard Procedure for Corneal Tissue Outgrowth Assay

Replicates, 20 mm diameter, of each polymeric sample are transferred to individual wells of a 6-well tissue culture polystyrene (TCPS) tray and left overnight at room temperature in a phosphate buffered saline solution containing 120 µg/ml penicillin and 200 µg/ml streptomycin. Each formulation assays in triplicate. Corneas are excised from freshly enucleated cow's eyes and the endothelium is carefully removed using jewellers forceps. Most of the stroma is then removed leaving an intact epithelial layer with approximately 10% of the stroma still attached. Tissue explant disks, of 6 mm in diameter, are cut from the remaining epithelial layer with a sterile biopsy punch and each one placed epithelial side up onto the center of each replicate polymer disk. The explants are cultured in the absence of serum in a culture medium consisting of Dulbecco's Minimal Essential Medium/Ham's F12 supplemented with 5 ug/ml insulin, 5 ug/ml transferrin, 5 ng/ml selenious acid, 60 ug/ml penicillin and 100 ug/ml streptomycin. Explants are cultured for a period of eight days at 37° C. in a humidified atmosphere of 5% CO$_2$ in air and the culture medium is changed at day three and day six. On day eight, the explants are stained with methylene blue (1% w/v in borate buffer pH 8.4) and outgrowth areas measured by image analysis (Quantimet 570, Leica Cambridge). A mean (±s.d.) tissue outgrowth index (MI) is calculated by dividing the final spread area of each explant by it's initial tissue area.

A tissue outgrowth index (Ml) of 100 denotes zero outgrowth and indicates that the material surface does not support tissue outgrowth.

| Support | % BCEp Cell (sd) Attachment and growth |
| --- | --- |
| Tissue culture polystyrene | 100 |
| Example 1 material | 42 |

The data indicate that the polymer supports the outgrowth of epithelial tissue over the surface of the polymer. The result also indicates that the polymer is generally biocompatible towards cells and tissue.

Wet Measurement of the Oxygen Permeability

The oxygen permeability of the material according to Example 1 is determined by the coulmetric method. The lenticules are clamped in a holder and the upper side of the lenticule is covered with a 2 cm layer of water. A gas mixture comprising 21% of oxygen and 79% of nitrogen is passed continuously through the water layer with swirling. The oxygen which diffuses through the lenticule is measured using a coulometric detector. The reference values are those measured on commercially available contact lenticules applying this method. Cibasoft® (CibaVision, HEMA lens) shows a values of approx. 7–10 barrer Excelens® (CibaVision, PVA lens) 22 barrer. The value obtained for the lenticules of Example 1 is 105 barrer.

What is claimed is:

1. Process for producing a porous polymer comprising the steps of:

(a) forming a composition comprising (i) a polymerizable component comprising at least one free radically polymerizable unsaturated monomer of formula

Q—X—A              (1), wherein Q is a radical of formula

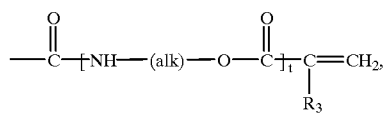

(2)

(alk) is linear or branched $C_2$–$C_{12}$-alkylene, $R_3$ is hydrogen or $C_1$–$C_4$-alkyl, and t is the number 0 or 1, X is a group —O—, —S— or —$NR_1$— and $R_1$ is hydrogen, $C_1$–$C_4$-alkyl or a radical A, and A is a radical of formula

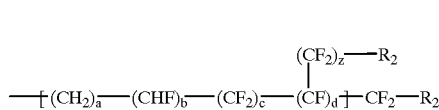

(3)

wherein $R_2$ is hydrogen or fluorine, a is an integer from 1 to 15, b is an integer from 0 to 6, c is an integer from 1 to 19, d is an integer of 0 or 1, and z is an integer from 1 to 12, and (ii) a solvent system being capable of effecting phase separation in the polymer which is obtained upon polymerizing the polymerizable component according to (i);

(b) polymerizing said composition and thereby forming a two-phase system comprising a polymer phase and a discrete solvent phase both of which are intermingled;

(c) removing the discrete solvent phase; and (d) subjecting the polymer obtained to an aftertreatment in an acidic or basic medium.

2. A process according to claim 1 wherein the polymerizable component comprises a least one monomer of formula (1), wherein Q is a radical of formula

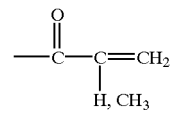

X is is —O—, and

A is a radical of formula

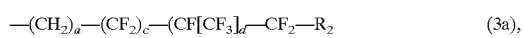

(3a), wherein $R_2$ is hydrogen or fluorine, a is an integer of 1 or 2, c is an integer from 1 to 19, and d is an integer of 0 or 1.

3. A process according to claim 1, wherein the polymerizable component comprises at least two different monomers of formula (1).

4. A process according to claim 1, wherein the polymerizable component in addition comprises one or more different crosslinkers.

5. A process according to claim 1, wherein the polymerizable component comprises a crosslinker of formula $Q_1$—PFPE—$Q_1$             (4a), wherein $Q_1$ is the methacryloyl or acryloyl radical, and PFPE is a radical of formula

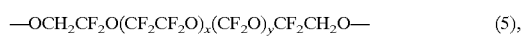

(5), wherein the $CF_2CF_2O$ and $CF_2O$ units may be randomly distributed or distributed as blocks throughout the chain, and x and y may be the same or different such that the weight average molecular weight of the perfluorinated polyether is in the range of from 500 to 2500.

6. A process according to claim 1, wherein the polymerizable component comprises a crosslinker of formula

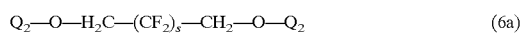

(6a)

or

(6b), wherein $Q_2$ is the methacryloyl or acryloyl radical, s is an integer from 1 to 10, and q is an integer from 1 to 20.

7. A process according to claim 1, wherein the polymerizable component comprises (i) at least two different monomers of formula

Q—X—A              (1)

and (ii) one or more different crosslinkers selected from the group consisting of a compound of formula

(4a), a compound of formula

(6a)

and a compound of formula

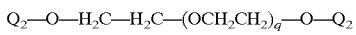

(6b);

wherein Q, $Q_1$ and $Q_2$ are each independently of the other a radical of formula

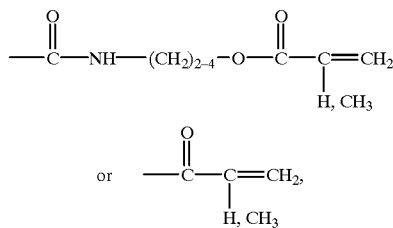

A is a radical of formula

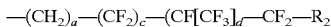

(3a), $R_2$ is hydrogen or fluorine, a is an integer of 1 or 2, c is an integer from 1 to 9 and d is 0 or 1, X is —O—, —NH— or —N($C_1$–$C_2$-alkyl), PFPE is a radical of formula

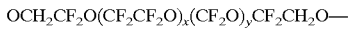

(5), wherein the $CF_2CF_2O$ and $CF_2O$ units may be randomly distributed or distributed as blocks throughout the chain, and x and y may be the same or different such that the weight average molecular weight of the perfluorinated polyether is in the range of from 500 o 2500, s is an integer from 4 to 8, and q is an integer from 1 to 4.

8. A process according to claim 1, wherein the solvent system (ii) according to step (a) comprises at least two components selected from the group consisting of a non-solvent, an intermediate solvent and a solvent for the respective polymerizable component (i).

9. A process according to claim 8, wherein the solvent is selected from the group consisting of a $C_5$–$C_{12}$-alkane, $C_5$–$C_{12}$-cycloalkane, benzene, $C_3$–$C_{10}$-ether and $C_3$–$C_{10}$-ketone, each of which unsubstituted or substituted by $C_1$–$C_4$-alkyl, $C_1$–$C_4$-alkoxy or halogen.

10. A process according to claim 8, wherein the intermediate solvent is selected from the group consisting of a non-fluorinated $C_1$–$C_{10}$-alkanol, $C_1$–$C_{10}$-amine, $C_1$–$C_{10}$-nitrile and a $C_1$–$C_{10}$-carboxylic acid.

11. A process according to claim 8, wherein the non-solvent is water.

12. A process according to claim 1, wherein the weight ratio of polymerizable component and solvent system is from 85%:15% to 50% to 50%.

13. A process according to claim 1, wherein in step (b) the polymerizable component is polymerized in the presence of a photoinitiator using UV radiation.

14. A process according to claim 1, wherein the after-treatment according to step (d) is carried out in a basic medium.

15. A process according to claim 14, wherein the after-treatment comprises treating the polymer in an basic medium for a time period from 30 seconds to 30 minutes at a temperature from 15 to 100° C.

16. A molding obtained by the process according to claim 1.

17. A molding according to claim 16 is a biomedical device.

18. A molding according to claim 16 is a medical implant.

19. A molding according to claim 16 is an ocular prostheses.

20. A molding according to claim 19 is an implantable intraocular lens or artificial cornea.

21. A molding according to claim 16 is a wound healing dressing.

22. A method of using a polymer that is obtainable by the process according to claim 1 as cell growth material, which comprises causing the polymer to interact with mammalian tissue cells.

23. A polymer which is the polymerization product of a composition comprising (i) at least two different monomers of formula (1) according to claim 1; and (ii) one or more different crosslinkers.

24. A polymer according to claim 23, wherein the composition comprises one or more different crosslinkers selected from the group consisting of a compound of formula

(4a), a compound of formula

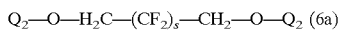

and a compound of formula

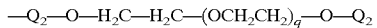

(6b);

wherein $Q_1$ and $Q_2$ are each independently of the other a radical of formula

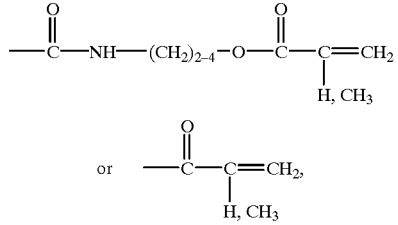

PFPE is a radical of formula

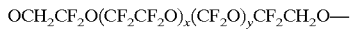

(5)

wherein the $CF_2CF_2O$ and $CF_2O$ units may be randomly distributed or distributed as blocks throughout the chain, and x and y may be the same or different such that the weight average molecular weight of the perfluorinated polyether is in the range of from 500 o 2500, s is an integer from 4 to 8, and q is an integer from 1 to 4.

25. A molding comprising a polymer according to claim 23.

* * * * *